(12) United States Patent
Fofonoff et al.

(10) Patent No.: US 6,281,007 B1
(45) Date of Patent: Aug. 28, 2001

(54) METHODS AND APPARATUS FOR THE CONDITIONING OF LIGAMENT REPLACEMENT TISSUE

(75) Inventors: Timothy W. Fofonoff, Dedham; Eugene Bell, Boston, both of MA (US)

(73) Assignee: TEI Biosciences, Inc., Boston, MA (US)

(*) Notice: Subject to any disclaimer, the term of this patent is extended or adjusted under 35 U.S.C. 154(b) by 0 days.

(21) Appl. No.: 09/396,255

(22) Filed: Sep. 15, 1999

Related U.S. Application Data

(62) Division of application No. 09/035,291, filed on Mar. 5, 1998, now Pat. No. 6,066,495.

(51) Int. Cl.$^7$ .................... C12N 5/00; C12M 3/00
(52) U.S. Cl. .................. 435/289.1; 435/395; 435/399
(58) Field of Search ................ 435/1.1, 1.2, 372, 435/373, 377, 395, 399, 401, 284.1, 297.2, 289.1; 623/11, 13, 16, 18

(56) References Cited

U.S. PATENT DOCUMENTS

| | | | |
|---|---|---|---|
| 4,485,097 | * 11/1984 | Bell . | |
| 4,835,102 | * 5/1989 | Bell et al. . | |
| 5,153,136 | 10/1992 | Vandenburgh | 435/284 |
| 5,266,480 | * 11/1993 | Naughton et al. . | |
| 5,406,853 | 4/1995 | Lintilhac et al. | 73/789 |
| 5,521,087 | 5/1996 | Lee et al. | 435/240.2 |
| 5,686,303 | 11/1997 | Korman | 435/325 |
| 5,700,688 | 12/1997 | Lee et al. | 435/287.1 |
| 5,792,603 | 8/1998 | Dunkelman et al. | 435/1.2 |
| 5,919,702 | * 7/1999 | Purchio et al. . | |
| 6,121,042 | * 9/2000 | Peterson et al. | 435/284.1 |

FOREIGN PATENT DOCUMENTS

WO 96/14452 5/1996 (WO) .

OTHER PUBLICATIONS

D. Huang et al., "Mechanisms and Dynamics of Mechanical Strengthening in Ligament–Equivalent Fibroblast–Populated Collagen Matrices," *Annals of Biomedical Engineering*, vol. 21, pp. 289–305 (1993).

E. Bell, Tissue Engineering: Current Perspectives, Birkhäuser, Boston, 1993.

K. Kanda et al., "Behavior of Arterial Wall Cells Cultured on Periodically Stretched Substrates," *Cell Transplantation*, vol. 2, pp. 475–484 (1993).

* cited by examiner

*Primary Examiner*—William H. Beisner
(74) *Attorney, Agent, or Firm*—Lahive & CockField, LLP

(57) ABSTRACT

Apparatus and methods are disclosed for maturing an elongate replacement tissue construct in vitro prior to use of the replacement construct in vivo as, for example, a ligament. The tissue is seeded with specific cells, exposed to a maturation fluid, and subjected to selected forces, which can include longitudinal stress, (i.e. stressing the tissue along its elongate axis). The tissue is disposed in a maturation chamber that confines maturation fluid for introduction to the tissue. A first mounting element couples to a first end of the elongate biopolymer tissue and a second mounting element couples to a second end of the tissue such that the tissue extends along a longitudinal axis, and a force is applied to at least one of the mounting elements for longitudinally stressing the tissue. The foregoing apparatus and methods are intended to provide a replacement tissue that is more readily integrable in vivo, i.e., a tissue that more readily degrades, regenerates and remodels in vivo to produce a more durable and functional replacement tissue.

55 Claims, 6 Drawing Sheets

METHODS AND APPARATUS FOR THE CONDITIONING OF LIGAMENT REPLACEMENT TISSUE

This application is a divisional application of Ser. No. 09/035,291 filed on Mar. 5, 1998, now U.S. Pat. No. 6,066,495. The contents of all of the aforementioned application(s) are hereby incorporated by reference.

BACKGROUND OF THE INVENTION

This application relates to the preparation of grafts, implants, prostheses or other tissue constructs, typically for use as replacements for damaged or diseased bodily tissue. More particularly, this application relates to apparatus and methods for maturing or conditioning biopolymer tissue constructs prior to implantation of the construct in the body.

Tissue constructs are often used as grafts, implants or prostheses to replace diseased or damaged bodily tissue. Tissue needing replacement can include, for example, cartilage, tendon and ligament tissue. A fully functional replacement tissue should withstand at least the stresses and strains imposed by normal bodily activity on the type of tissue the construct is to replace. Furthermore, the construct should be biocompatible and integrable, in vivo, i.e., the construct should resemble a natural tissue so as to attract and interact with specific cells present in the body. The attracted cells further organize the construct and secrete specific biosynthetic products, such as extracellular matrix proteins and/or growth factors, that bind to the replacement construct, enabling it to degrade, remodel and regenerate as a fully functional replacement tissue. Such integration strengthens and conditions the construct to better perform as a replacement tissue.

Synthetic materials such as polyester fibers (Dacron™) or polytetrafluorlethylene (PTFE) (Teflon™) have been used extensively as replacements for bodily tissue, with some success. However, due to the poor biocompatibility of such synthetic materials, they often initiate persistent inflammatory reactions. Additionally, they do not readily breakdown and are not readily integrated with the body via remodeling by tissue cells.

It is also known to fabricate replacement constructs from structural biopolymer matrix components, such as collagen, that are extracted, purified and combined with specialized cells. The cells can organize, condense, and otherwise interact with the matrix proteins to create a tissue-like construct that can more closely resemble a natural tissue, and hence more readily integrate with the body than implants, grafts or prostheses based on synthetic materials. However, available biopolymer implants do not always have, or develop in vivo, the matrix complexity characteristic of the tissue they are to replace so as to become fully-functional replacements.

Therefore, there is a need for improved replacement tissue constructs that are stronger and more readily integrable with the bodily environment. Accordingly, one object of the invention is to provide methods and apparatus for producing improved replacement tissue constructs.

Another object of the invention is to provide replacement tissue constructs that are stronger and more capable of withstanding the stresses and strains imposed thereon by the rigors of bodily activity.

A further object of the invention is to provide apparatus for maturing and conditioning prostheses, grafts and implants to be more readily accepted by and integrable with the natural bodily environment.

Another object of the invention is to provide prostheses, grafts and implants that more readily resemble the tissues they are intended to replace.

Other general and more specific objects of the present invention will in part by obvious and will in part appear from the drawings and description which follow.

SUMMARY OF THE INVENTION

The present invention attains the foregoing and other objects by providing methods and apparatus for exposing elongate biopolymer tissue constructs to selected conditions, i.e., to a selected maturation fluid and to selected forces and/or stresses, for maturing the replacement tissue prior to insertion of the tissue into the body. Typically the elongate tissue construct is intended for use as a replacement ligament tissue. The elongate biopolymer tissue constructs described herein typically includes biopolymer fibers. Methods and apparatus for fabricating biopolymer fibers are known to those of ordinary skill in the art as disclosed in U.S. Pat. No. 5,562,946, entitled "Apparatus and Method for Spinning and Processing Collagen Fiber," issued Oct. 8, 1996, the disclosure of which is herein incorporated by reference.

As used herein, maturing a tissue refers to conditioning a tissue such that it is more readily integrable with the bodily environment. An integrable tissue is a tissue that more readily remodels, degrades and regenerates within the body to create a stronger and more durable functional replacement tissue. Maturing a tissue construct can also refer to increasing the mechanical strength of the tissue such that it more readily withstands the stresses and strains of bodily activity.

As used herein, a biopolymer is a polymer suitable for introduction into a living organism, e.g., a human. The biopolymer is usually non-toxic and bioabsorbable when introduced into the living organism, and any degradation products of the biopolymer are also non-toxic to the organism. The biopolymer can be formed into biocompatible constructs that include, for example, biopolymer foams, e.g., single or double density foams, and/or biopolymer fibers. A typical biopolymer is collagen.

Typically, a biopolymer tissue construct to be matured using the apparatus and methods of the present invention is seeded with cells, such as connective tissue cells obtained from a biopsy of human or animal tissue. Exposing the replacement tissue to maturation fluid and subjecting the tissue to selected forces is believed to provide an environment that, similar to the natural bodily environment, provides biological signals to the seed cells for producing an integrable replacement tissue more readily accepted by the body. For example, the biological signals provided by the methods and apparatus of the present invention may promote, in addition to other beneficial effects, the secretion of extracellular matrix material, the generation of cell binding sites that attract specific cells from the body, or cell differentiation.

The maturation and seeding fluid is typically a fluid that resembles the naturally occurring fluid present in the bodily environment in which the tissue is to be used. The present invention is intended to be particularly useful in maturing replacement ligament tissue. For example, the maturation fluid can be a tissue culture media with suitable biological supplements. The maturation fluid can have several functions, which can include at least one of the following: delivering seed cells to the replacement tissue, delivering nutrients to the seed cells to promote expansion of the seed cell population, delivering growth factors to the replacement tissue to promote the generation of extracellular matrix material, as well as other functions that those of ordinary skill in the art, in light of the disclosure herein, can appreciate. The invention is intended to be particularly useful for the maturation of replacement ligament tissue.

According to one aspect, the invention provides apparatus that includes an element for extending the elongate biopolymer tissue construct along a longitudinal axis, an element for introducing a maturation fluid to the elongate tissue to promote tissue maturation, and an element for applying a selected force to the tissue construct to promote tissue maturation. The extending element can include first and second mounting elements for coupling to first and second ends, respectively, of the elongate biopolymer tissue, thereby mounting the tissue so as to extend between the mounting first and second mounting elements. In one aspect of the invention, the mounting elements can include a weight for coupling to one end of the elongate tissue construct. In another aspect of the invention, the mounting elements include a piston disposed in a longitudinal bore in which the tissue construct can be disposed.

In yet a further aspect of the invention, the fluid element includes a housing having a bore therethrough for confining maturation fluid and for mounting the elongate tissue therein. In another aspect of the invention, the fluid element includes a reservoir for confining the maturation fluid.

In another aspect of the invention, the force element includes apparatus for applying a longitudinal stress, i.e. a stress along the elongate axis of the tissue, to the tissue, by for example, applying a longitudinally directed force to one of the mounting elements. The force element can also include an element for applying a force, in a direction transverse to the longitudinal axis, to at least a portion of the elongate tissue construct. The transverse force element can be a weighted element suspended from the elongate tissue, and position-varying elements can be included for tilting and rotating the elongate tissue construct, (e.g. by tilting and rotating the maturation chamber in which the tissue is disposed) thus varying the portion of the tissue construct to which the transverse force is applied. Typically, tilting the tissue translates the weighted device along the length of the elongate tissue and rotating the tissue varies the position of the weighted device. In another aspect of the invention, the transverse force element can include a magnetic device coupled to the elongate tissue construct, and elements can be included for subjecting the magnetic device to selected magnetic fields so as to apply a selected transverse force to the tissue.

In a further aspect of the invention, the force element includes an element for applying selected frictional forces to the surface of the tissue construct. For example, the weighted device, or the magnetic device discussed above, can include a surface for contacting the tissue construct so as to apply a selected frictional force as the position of the device is varied along the length of, and around the circumference of, the tissue construct.

In one embodiment of the invention, apparatus according to the invention includes a housing having a bore formed therein, the bore extending along a longitudinal axis and having a first end and a second end; an endcap for sealing the first end of the bore; a piston adapted for longitudinal travel in at least a portion of the bore, the piston and the endcap defining a first bore volume bounded in part by the endcap and the piston; elements for coupling a first end of the tissue to the piston and for coupling a second end of the tissue to the endcap such that the tissue is disposed in the first bore volume and along the longitudinal axis, and means forming at least a first fluid port in the housing for transferring maturation fluid with the first bore volume for promoting maturation of the tissue. The apparatus can also include a second endcap for sealing the second end of the bore, the piston and the second endcap defining a second bore volume bounded in part by the piston and the second endcap, means forming an additional fluid port in the housing for transferring fluid with the second bore volume, and the piston can include a throttling orifice therethrough for providing selected fluid communication between the first bore volume and the second bore volume.

The present invention can include, for use with the above embodiment, and as appropriate with other embodiments disclosed herein or variations thereof, a fluid supply element for providing a maturation fluid. For example, in the above embodiment, the fluid supply element can supply maturation fluid to one of the first and additional fluid ports and draw the fluid from the other of the ports, thereby generating maturation fluid flow in the first and second bore volumes and through the throttling orifice. The fluid supply element can thus provide a selected fluid flow such that the throttling orifice creates a pressure differential between maturation fluid in the first bore volume and the second bore volume for acting on the piston and placing a selected longitudinal stress on the tissue. The flow of maturation fluid can be cyclically modulated for placing a selected cyclical longitudinal stress on the tissue.

In another embodiment, the invention includes a housing having a longitudinal bore formed therein for confining a maturation fluid and for housing the elongate biopolymer tissue construct, the tissue construct is extended along the longitudinal axis of the bore, and a coupling element for coupling a first end of the elongate biopolymer tissue to the housing is attached. A weight element couples to the other end of the elongate tissue for applying longitudinal stress thereto. Finally, an element for tilting the housing for varying the portion of the gravitational force on the weight applied to the elongate biopolymer tissue is employed, thereby varying the longitudinal stress applied to the tissue. The weight can include a fluid bypass element for allowing maturation fluid to pass by the weight when the weight is disposed within the bore. The fluid bypass element can include at least a first recessed face of the weight for providing a selected gap between the face and the wall of the bore.

Forces need not be applied to the replacement tissue construct throughout the maturation process, nor need the composition of the maturation fluid remain constant. For example, for expansion of the seed cell population, the maturation fluid can contain cell nutrients. During expansion of the seed population, forces are typically not applied to the replacement tissue. However, to provide biosignals to promote cell differentiation and/or secretion of the extracellular matrix material, forces are typically applied and cell nutrients are of lesser importance as a component of the maturation fluid, than for example, growth factors for promoting proper cell differentiation. Thus the apparatus and methods of the present invention are intended to provide a versatile tissue-maturation tool that one of ordinary skill in the art, based on the disclosures herein, can use to tailor the conditioning of a replacement tissue. According to the invention, tissue can be matured not only for implantation but as part of a research study, in which case the exact program of forces and maturation fluid composition could be varied to determined the effect on tissue development. Research efforts may result in an improved or optimized program that is then applied to the maturation of tissue constructs for use in vivo.

The invention also includes methods practiced in accordance with the teachings of the invention presented herein.

BRIEF DESCRIPTION OF THE DRAWINGS

The foregoing and other objects, features and advantages of the invention will be apparent from the following description and apparent from the accompanying drawings, in which like reference characters refer to the same parts throughout the different views. The drawings illustrate principles of the invention and, although not to scale, show relative dimensions.

DETAILED DESCRIPTION OF THE ILLUSTRATED EMBODIMENTS

Figure 1:
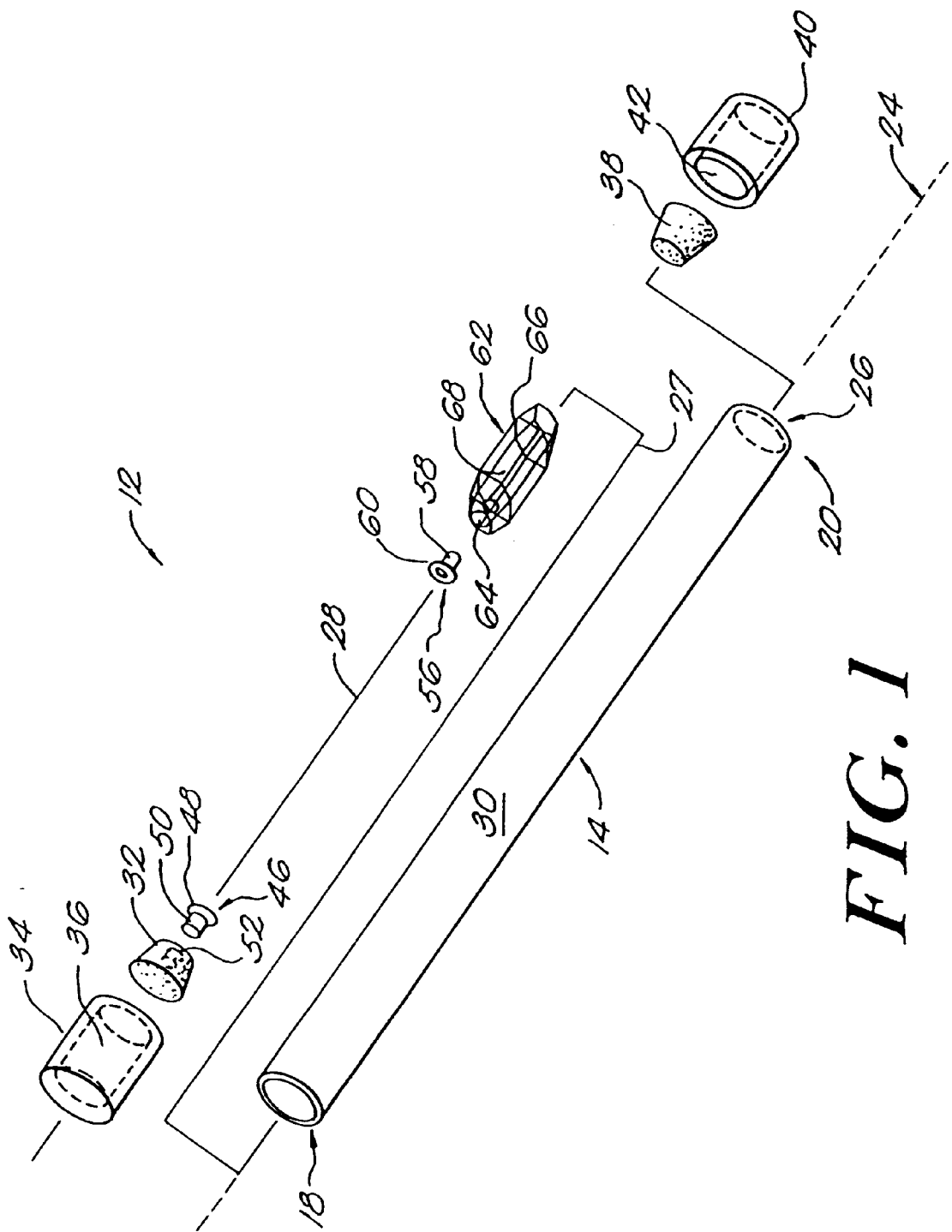
FIG. 1 shows an exploded, perspective view of one embodiment according to the invention of a maturation chamber for maturing an elongated biopolymer tissue.

FIG. 1 shows a maturation chamber 12 for maturing biopolymer replacement ligament tissue prior to, for example, implantation of the ligament in the human body. The illustrated tissue maturation chamber 12 includes a tubular housing 14 extending from a first end 18 to a second end 20 along a longitudinal axis 24, and having a longitudinal bore 26 extending therethrough. As indicated by connection line 27, the elongated biopolymer tissue 28 is disposed within the bore along longitudinal axis 24.

A stopper 32 inserts into the first bore end 18 of the housing 14. A first end of the biopolymer tissue 28 is attached to a nylon screw 48 which seats within an aperture 52 formed in a front surface of the stopper 32, thereby coupling the tissue 28 to the housing 14. Similarly, the tissue 28 is coupled to a weight 62 by a nylon screw 58. Specifically, the screw 58 threads into a threaded aperture 64 formed in one surface of the weight 62. The illustrated weight 62 is hexagonally shaped to contact the wall of the bore 26 along selected portions, such as along lines 66, while concomitantly allowing the weight to move freely within the bore 26. The hexagonal shape further forms fluid passages that allow fluid in the bore 26 of the housing 14 to pass along the outer surface of the weight through gaps formed between the inner wall of the housing 14 and the recessed faces 68 of the weight 62.

The endcaps 34 and 40 include apertures 36 and 42, respectively, that fit over the first and second housing ends 18 and 20, and over the stoppers 32 and 38, respectively. The stoppers 32 and 38 and the endcaps 34 and 40 confine a maturation fluid 30 within the bore 26 of the housing 14 and introduce the maturation fluid 30 to the elongate biopolymer tissue 28 disposed within the bore 26. The endcaps 34 provide an extra measure of security against unwanted leakage of the maturation fluid from the bore 26 of the housing 14, and also help to maintain the sterility of the maturation fluid 30 and of the elongate biopolymer tissue 28.

Figure 2:
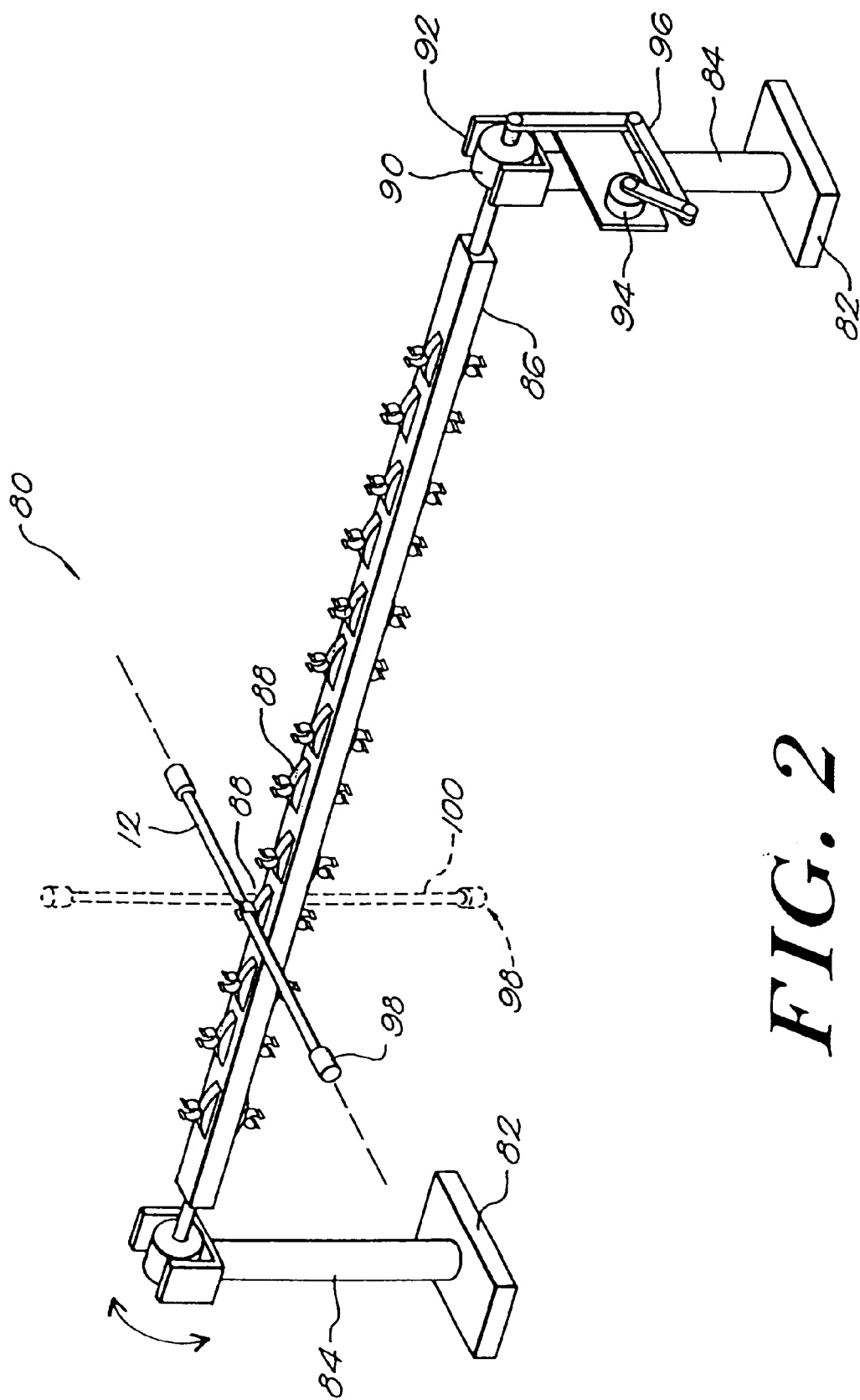
FIG. 2 shows a perspective view of apparatus for supporting and tilting the maturation chamber of FIG. 1 to apply a selected longitudinal stress to the elongated biopolymer tissue.

FIG. 2 illustrates an apparatus 80 for supporting and tilting the maturation chamber 12 for applying a selected longitudinal stress to the elongate biopolymer tissue 28 disposed therein. Tilting the maturation chamber 28 from the horizontal position, shown in FIG. 2, to the illustrated vertical position 100, shown in phantom, varies that portion of the gravitational force on the weight 62 that is borne by the biopolymer tissue 28, and hence the longitudinal stress applied to the elongate tissue 28. For example, when the chamber 12 is disposed in the vertical position 100, the weight 62 is fully suspended by the tissue 28 and the longitudinal stress placed on the tissue 28 is at a maximum. However, when the chamber 12 is disposed in the horizontal position, the wall of the housing 14 supports the weight and little or no stress is placed on the tissue 28. At positions in between vertical and horizontal, the portion of the gravitational weight borne by the elongate tissue 28 varies, as is understood by one of ordinary skill in the art, as a sinusoid.

The illustrated chamber manipulation apparatus 80 includes a series of clips 88 that couple one or more maturation chambers 12 to a rotatable support rod 86. The roller 90 and the roller seat 92 constitute a bearing that rotationally couples the support rod 86 to the support posts 84 and the support platforms 82. A mechanical linkage assembly 96 includes a motor 94 that is mounted on one of the support posts 84. The motor is further coupled to the support rod 86 for cyclically rotating the chamber 12, as indicated by path 98, between the horizontal position and the vertical position, as illustrated.

A typical regimen for maturing an elongate biopolymer replacement tissue for potential use as a ligament involves cycling the chamber 12 from the horizontal to the vertical position at a selected rate, such as approximately 1 to 10 cycles per minute, for a selected period of time, such as between a few minutes to as long as a few weeks. According to a preferred practice, the apparatus 80 is disposed in an incubator that is maintained at a temperature of about 98.6° F. The maturation fluid in the tissue maturation chamber 12 is changed approximately every other day. The apparatus 80 can include a plurality of clips for mounting multiple maturation chambers 12.

The apparatus and methods of the invention are intended to facilitate maturation of elongate biopolymer constructs for use as, for example, ligament replacement tissues. As appreciated by one of ordinary skill in the art, in light of the disclosures herein, the apparatus and methods of the present invention are useful in maturing a variety of tissue constructs. For example, tissue constructs can include biopolymer fibers, biopolymer foams, or a combination of fibers and foams. The fibers can be braided or spun in a variety of ways.

In one example, the weight 62 is hexagonally shaped, about 4 cm long, weighs about 5 grams and is fabricated from Teflon. The housing 14 is made of polycarbonate and extends for about 20 inches along the longitudinal axis 24. The bore 36 has a diameter of approximately 0.5 inch, to which the weight is closely fit. The faces 68 create a 3 mm to 4 mm fluid bypass gap between a face 68 of the weight and the inner wall of the housing 14 that bounds the bore 26. The tissue construct 28 includes a number of collagen fibers braided together, such as for example eight. The biopolymer tissue construct can be encapsulated by a biopolymer foam tube (not shown) to prevent or inhibit the maturation fluid from washing away growth factors and other products secreted by the cells seeded in the elongate biopolymer construct. The biopolymer foam tube can form part of the biopolymer replacement ligament.

The biopolymer tissue is subjected to longitudinal forces that apply a force or stress to the tissue. In this manner, the tissue is stretched an amount between about 1% and about 20%, preferably between about 2% and about 10%, and most preferably between about 2% and about 5%. 54. The magnitude of the force applied to the tissue is between about 0.2 Mpa (megapascals) and about 10 Mpa. those of ordinary skill will recognize that the amount of stress or force applied to the tissue depends upon a number of factors, including the amount of cross-linking that occurs within the tissue and upon the overall strength of the material.

Figure 3:
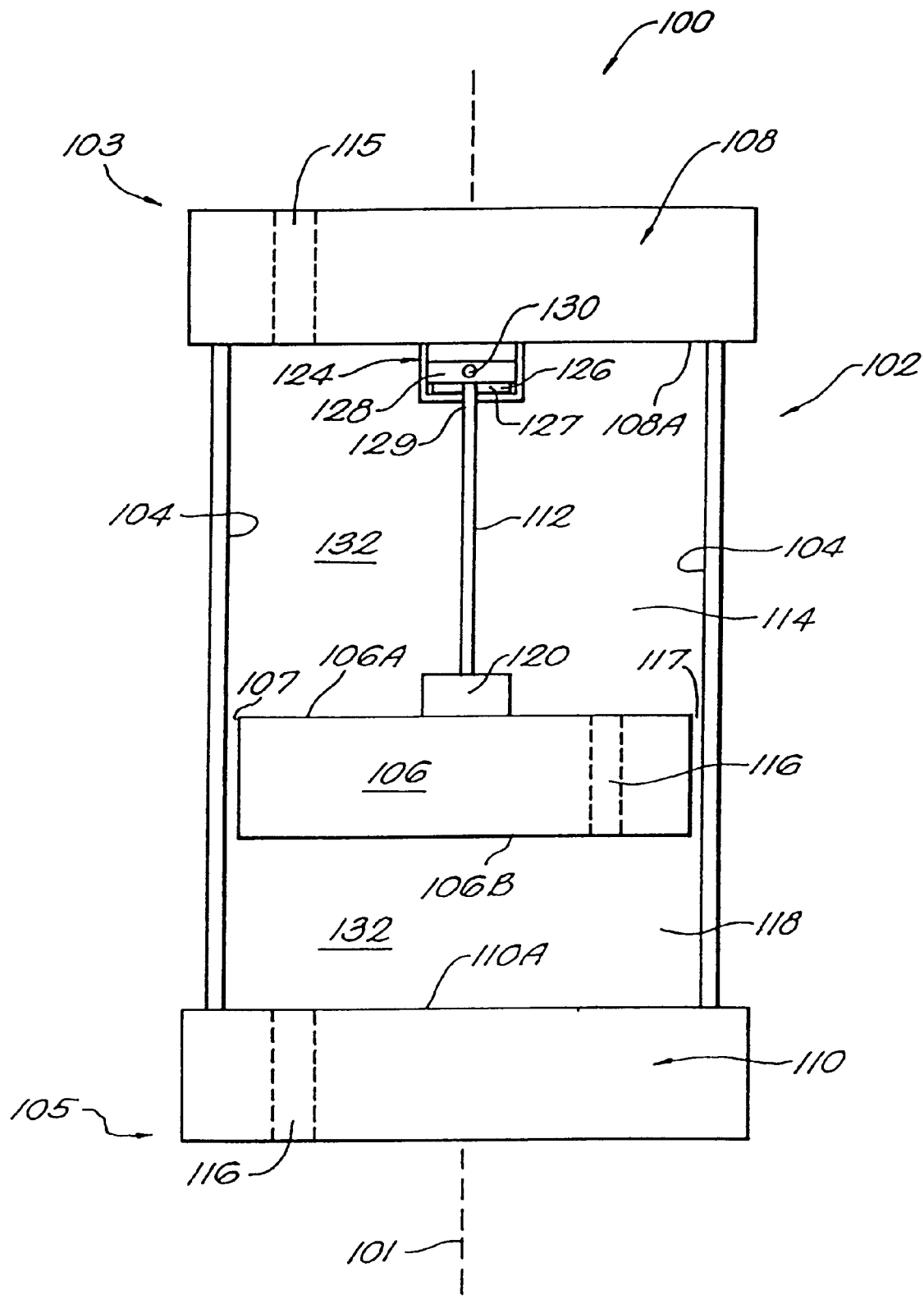
FIG. 3 shows another embodiment according to the invention of a tissue maturation chamber for maturing an elongated biopolymer tissue.

FIG. 3 shows another embodiment of the tissue maturation chamber 100 of the invention for maturing an elongated biopolymer tissue. The illustrated tissue maturation chamber 100 includes a housing 102 which extends from a first end 103 to a second end 105 of the housing along a longitudinal axis 101. A piston 106 is disposed for longitudinal travel in a longitudinal bore formed by housing walls 104. The housing includes endcaps 108 and 110 for sealing the first and second ends of the housing 102.

The illustrated endcap 108 includes a fluid port 115 for transferring a maturation fluid with a first bore volume, designated as 132, into a first chamber 114 bounded by the upper surface 106A of the piston 106, the inner wall 104 of the housing 102, and the rear surface 108A of the endcap 108. The endcap 110 also includes a fluid port 116 that spans between front and rear surfaces of the endcap for transferring maturation fluid 132 into another chamber 118, which is bounded by the lower surface 106B of the piston 106, the housing wall 104, and the front surface 110A of the endcap 110. The piston 106 includes a throttling orifice 116 for transferring maturation fluid between the first chamber 114 and the second chamber 118, and for creating a pressure differential therebetween. The pressure differential between the first and second chambers 114 and 118 creates a force on the piston 106 which is transferred to the tissue, thereby applying a longitudinal stress thereto. This longitudinal stress conditions or matures the tissue when in contact with the maturation fluid and when housed within the maturation chamber 100 in order to better adapt to the rigors and to the biological environment of the host. Those of ordinary skill will recognize that the piston can be sized such that its circumferential surface is spaced a selected amount from the inner wall 104 of the housing 102. The gap formed therebetween forms also allows a selected degree of leakage between the chambers 114, 118, and thus function as a secondary throttling valve 117. The gap 117 and the orifice 116 can be dimensioned to provide a selected degree of force to the tissue to condition the tissue according to a selected regimen. An ordinarily skilled artisan knowing the type of tissue, cells, and maturation fluid, as well as the type of implant the tissue is to replace, can construct an appropriate conditioning regimen, and thus be able to determine the amount and duration of the force to be applied to the tissue. According to an alternate embodiment, the piston is free of any throttling valve, and the differential force is created only by the gap formed between the inner wall 104 and the piston 106.

A piston mounting element 120 couples to one end of the elongate biopolymer tissue 112 housed within the first chamber and to the piston 106 at the other end. Further, a mounting element 124 couples to the rear surface 108A of the endcap 108 for mounting the other end of the tissue, thereby disposing the elongate biopolymer tissue 112 so as to extend along the longitudinal axis 101. The illustrated mounting element 124 includes a recess 128 sized and dimensioned for receiving a washer 126 having a central aperture through which the an end of the elongate biopolymer tissue 112 passes. A knot 130 tied in the tissue 112 is larger than the washer aperture 127 and secures the elongate biopolymer tissue 112 to the washer 126. The bottom of the mounting element 124 includes a slot 129, through which the elongate biopolymer tissue passes. The illustrated mounting and fastener assemblies 124 and 120 couple the tissue to the endcap and to the piston to apply a longitudinal force thereto.

The force applied to the tissue can be varied in a number of ways, including by varying or adjusting the fluid pressure between chambers 114 and 118. The resultant differential pressure can apply a dragging or downward force on the piston and thus to the tissue. The differential pressure can be varied by applying a vacuum assembly to the passage 116 to vary the fluid transfer rate between the chambers 114 and 118. The different transfer rates disposes the chambers at different pressure, thus varying the force applied to the tissue by the piston. Other methods include mechanically coupling the piston to an external device capable of selectively pulling the piston in the longitudinal direction. The introduction rate of the maturation fluid into the chamber 114 can also be varied. Other methods will be obvious to the ordinarily skilled artisan in light of the teachings herein.

In operation, the tissue is coupled to the washer 126 at one end and to the piston fastener 120 at the other end. The washer is then mounted within the recess 128 of the mounting element 124 to secure the tissue to the system 100. The maturation fluid is then introduced, for example, to the chamber 114 through the bore 115 formed in the endcap 108. The maturation is purged from the chamber 118 through orifice 116 formed in the endcap 118. The fluid is conveyed between the chambers 114 and 118 through either or both of the throttling passages 116 and 117. The maturation fluid delivers seed cells, nutrients and growth factors to the tissue to promote expansion of the seed cell population and to promote the generation of extracellular matrix material. The longitudinal stress applied to the tissue by the weight of the piston subjects the maturing tissue to forces similar to those that the tissue can expect to be exposed to when placed within the host.

Figure 4:
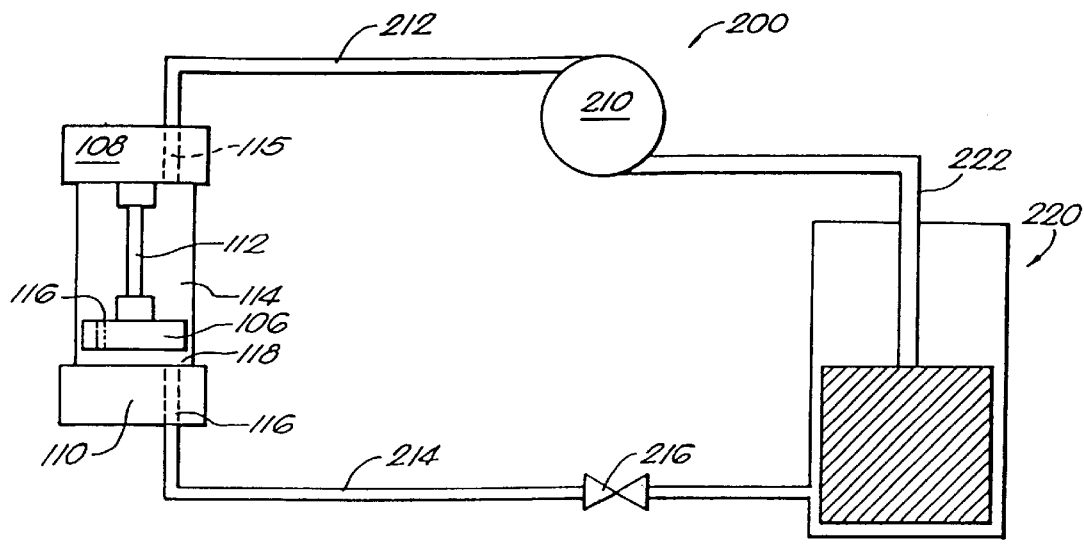
FIG. 4 shows a maturation fluid supply system for supplying fluid to and for actuating the tissue maturation apparatus shown in FIG. 3, and in FIGS. 8A, 8B, and 8D.

FIG. 4 illustrates one example of a fluid supply system 200 suitable for supplying maturation fluid to, and variably actuating, the tissue maturation chamber 100 so as to provide a longitudinal stress on the elongated biopolymer tissue 112. The illustrated system 200 includes a reservoir 220 that contains a quantity of maturation fluid 218, a variable speed pump 210, a throttling valve 216, and fluid conduits 212, 214, and 222. The fluid conduit 214 couples the passage 116 formed in the endcap 110 with the valve 216 and with the reservoir 220. The reservoir in turn is connected to the variable speed pump 210 through conduit 222, and with the maturation chamber 100 through conduit 212. The illustrated variable speed pump 210 cyclically varies the flow of maturation fluid 218 from the reservoir 220 to the chamber 114 through the endcap passage 115. The valve 216 regulates or varies the flow of maturation fluid out of the chamber 118. 55. The longitudinal stress is cyclically applied to the tissue in the range between about 1 and about 30 cycles per minute.

In operation, the maturation fluid 218 is introduced to the chamber 114 by the pump 210 through the passage 115. The maturation fluid fills the chamber 114 and passes through the throttling orifice 116, and other orifice, into the chamber 118. The difference between the rate of fluid introduction to the chamber 114 by the pump 210 and the rate of fluid removal from the chamber 118 as dictated by the valve 216 defines the overall force applied to the piston. Specifically, the difference in pressure between the two chambers creates a pressure differential on the piston that cyclically varies with the cyclical flow created by the variable speed pump 210. A cyclical pressure is thus applied to the piston 106, which in turn creates a cyclical longitudinal stress on the elongated maturation tissue 112. The throttling valve 216 and the valve 216 can be used to select or limit the cyclical pressures to a preselected range.

Figure 5A:
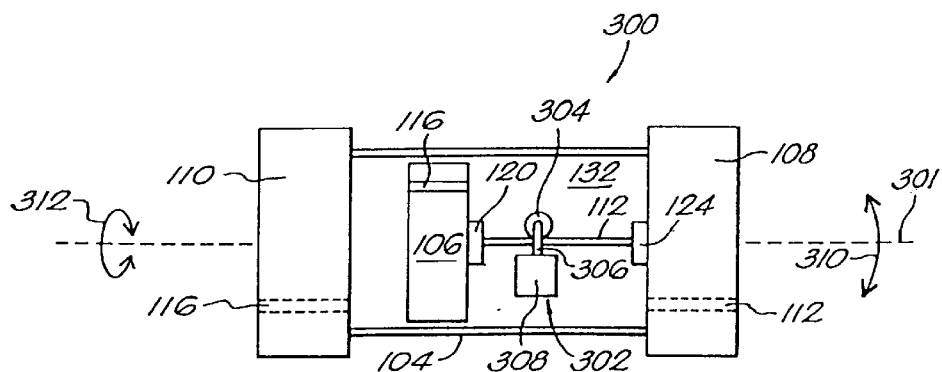
FIGS. 5A and 5B illustrate a weighted apparatus for use with the tissue maturation chambers shown in FIGS. 3 and 4 for applying a transverse force to the elongated biopolymer tissue.
Figure 5B:
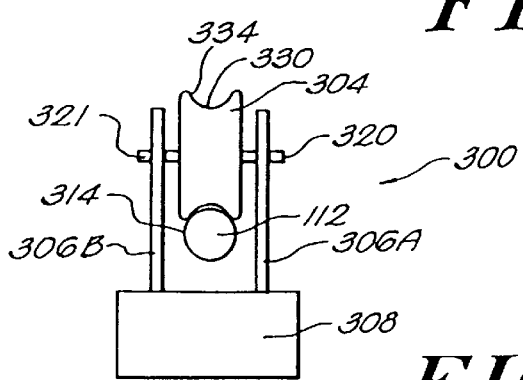

FIGS. 5A and 5B illustrate another system for applying a different type of force to the tissue 112. The illustrated system 300 includes the maturation chamber 100 previously described, but with a weighted device 302 disposed within and suspended from the biopolymer tissue 112. The weighted element 302 can apply a force to the tissue 112 in a direction transverse to the longitudinal, or elongate, axis of the tissue for maturing the tissue. The weighted element 302 includes a roller 304 having a contact surface 330 for engaging the tissue 112, and shoulders, such as shoulder 334, for guiding and thus retaining the roller 304 on the tissue 112. An axle pin 320 rotationally couples the roller 302 to a pair of support arms 306A and 306B, which straddle the elongate tissue 112, and which couple the roller 302 to a selected weight 308.

The transverse force applied to the tissue 112 by the weighted element 304 applies can be varied by providing an element or elements for tilting the maturation chamber 300 back and forth, as indicated by path 310, so as to translate the weighted element 302 to translate along the length of the elongate tissue 112. A suitable system for effectuating this tilting is the tilt apparatus 80 of FIG. 2. The portion of the tissue 112 that contacts the roller 304, and to which the transverse force is applied, is thus varied along the length of the tissue. The portion of the tissue to which the transverse force is applied can be circumferentially varied about the circumference 314 of the elongate tissue 112 by rotating the maturation chamber 300 about the longitudinal axis 301, as indicated by rotational path 312.

Figure 6:
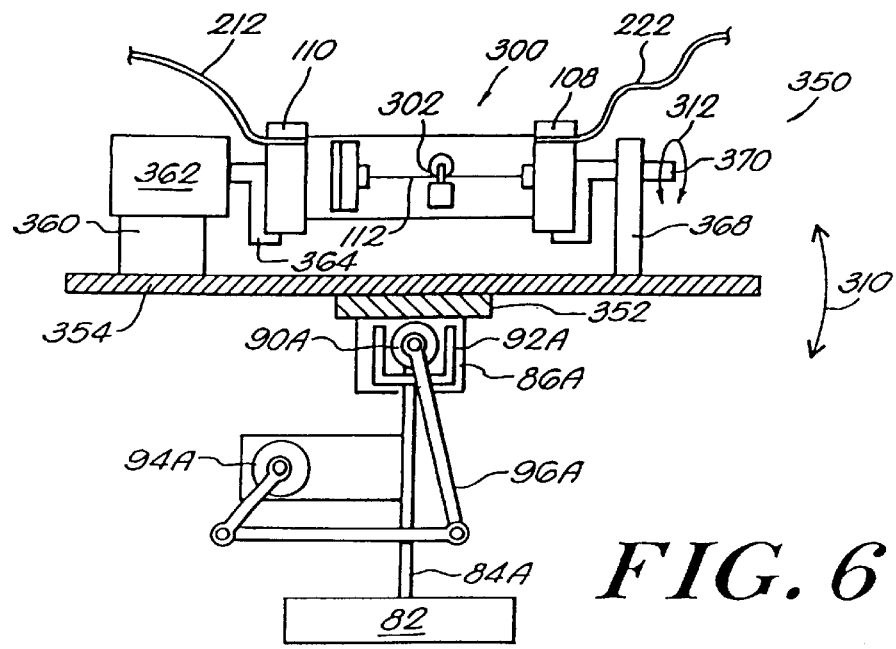
FIG. 6 illustrates one apparatus for tilting and rotating the tissue maturation chamber of FIGS. 5A and 5B for translating the weighted apparatus disposed therein along the elongated biopolymer tissue.

Another suitable apparatus for tilting and rotating the maturation chamber 300 is illustrated in FIG. 6. The illustrated apparatus 350 can be similar, in certain respects, to the apparatus 80 of FIG. 2. The clips 88 shown in FIG. 2 are replaced by a mounting bracket 352 that mounts a support plate 354. The support plate 354 supports a support post 368 and a motor bracket 360 that supports a second motor 362. L-shaped bracket 364 couple the motor 362 to the endcap 110 of the tissue maturation chamber 300. A second L-shaped bracket couples to the endcap 108 and is rotationally supported by the support post 368. Flexible conduits 212 and 222 convey a maturation fluid to and from a fluid supply apparatus, such as apparatus 200 discussed in conjunction with FIG. 4. The second motor thus rotates the maturation chamber 300 about the longitudinal axis 351 for circumferentially varying the portion of the tissue to which the weighted device 302 applies the transverse force. Typically, the second motor will periodically or selectively reverse direction to cyclically rotate the L-shaped brackets 364 and 370 in a plane that corresponds to a plane that extends into and out of the page.

As in the apparatus shown in FIG. 2 for tilting the maturation chamber 12, the roller 90A and roller seat 92A rotationally couple the support rod 86A to the support posts 84A and to the support platforms 82A. The linkage 96A couples a motor 94A, mounted on one of the support posts 84A, to the support rod 86A for tilting the support rod 86A, and hence the maturation chamber 300, back and forth, as illustrated by path 310. This movement translates the weighted device 302 back and forth along the elongate tissue 112. The linkage 96A and the motor 94A thus differ from the linkage 96 and from the motor 94 of FIG. 2 in that the support rod is tilted back and forth so as to appropriately translate the weighted device 302, as desired, along the elongate biopolymer tissue 112, rather than rotating the maturation chamber 300 from horizontal to vertical.

Figure 7A:
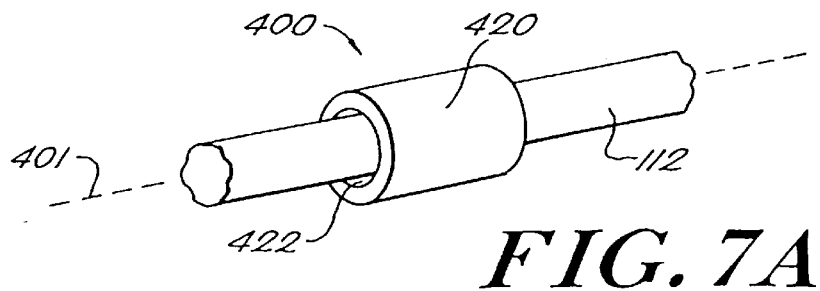
FIGS. 7A and 7B show an alternative embodiment of the maturation chamber for applying a transverse force to the elongated biopolymer tissue.
Figure 7B:
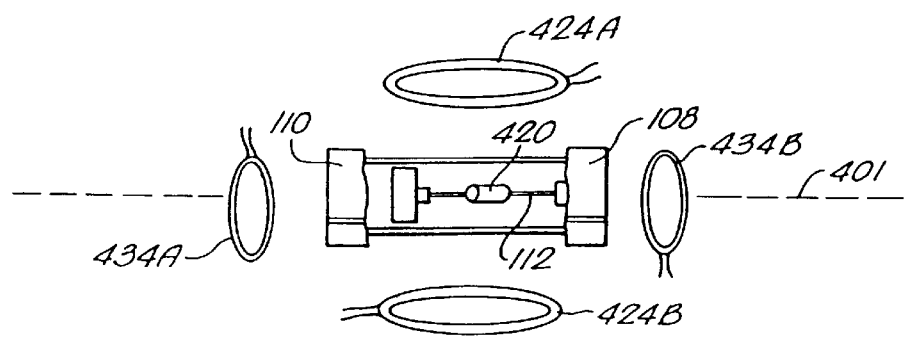

FIGS. 7A and 7B illustrate still another embodiment of an apparatus for applying a force to the tissue 112 transverse to the longitudinal axis 401. A magnetic device, such as a ferromagnetic tubular cylinder 420, is disposed and rests on the tissue 112. The tubular cylinder 420 has an inner wall 422 defining an inner lumen through which the biopolymer tissue 112 passes. As illustrated in FIG. 7B, a first pair 424 of Helmholtz coils 424A and 424B are disposed above and below the maturation chamber, and a second pair 434 of Helmholtz coils 434A and 434B are disposed on either side of the chamber, along the longitudinal axis 401. As appreciated by one of ordinary skill in the art, applying appropriate current to the first pair of coils produces a magnetic field at the tissue 112 which acts upon the tubular cylinder 420. The strength and direction (i.e. up or down in FIG. 7B) of that force can be varied by altering the current in the coils 424. The total force applied to the tubular cylinder 420 can be varied between, for example, an upward or downward force on the tissue, to apply a transverse force to the tissue 112 disposed within the lumen of the magnetic device 420.

The second pair of coils 434 establish a magnetic field along the longitudinal axis 401, and hence force the magnetic device 420 to shuttle along the outer portion of the tissue along axis 401. Again, as appreciated by one of ordinary skill, the magnitude and direction of the current in the pair of coils 434A and 434B can be controlled to translate the magnetic device back and forth along the length of the elongate tissue 112.

As one of ordinary skill will recognize, the magnetic device 420 can be translated by tilting the maturation chamber as an alternative to the use of the field coils 434. Furthermore, rotating the maturation chamber, as portion of the apparatus displayed in FIG. 6 can vary circumferentially about the tissue 112 the portion of the tissue to which the transverse force is applied.

Figure 8A:
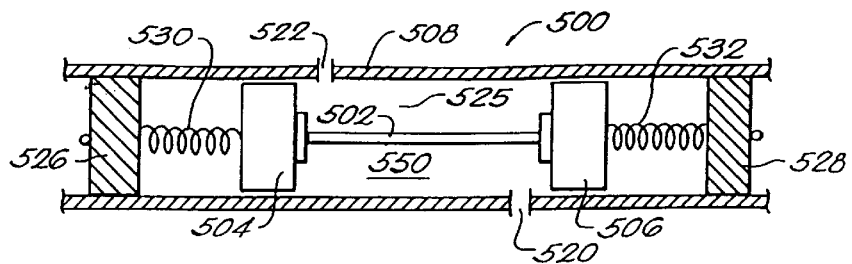
FIGS. 8A through 8D illustrate the principal features of alternative embodiments of the tissue maturation apparatus of previous figures for maturing an elongate biopolymer tissue in accordance with the teachings of the present invention.

FIGS. 8A through 8D illustrate yet other embodiments of the tissue maturation chamber of the present invention. FIG. 8A illustrates a tissue maturation apparatus 500 for mounting an elongate biopolymer tissue 502 between pistons 504 and 506 disposed for translation in a longitudinal bore formed by housing wall 508. Fluid ports 520 and 522 provide for a flow of maturation fluid 550 into the bore volume 525 and for providing a fluid pressure on pistons 504 and 506 for longitudinally stressing the elongate biopolymer tissue 502. Optional end caps 526 and 528 support return springs 530 and 532 respectively for facilitating the relaxation of the longitudinal stress on the tissue 502 when the pressure of the maturation fluid 550 is reduced in the bore volume 525. Accordingly, when the central chamber formed between the pistons 504 and 506 fills with maturation fluid, the pistons slidingly move outwardly toward the ends of the apparatus 500, thereby exerting a longitudinal stress on the tissue. The fluid inflow through bore 522 and the fluid outflow through bore 520 can be controlled so as to apply varying degrees of force on the tissue.

Figure 8B:
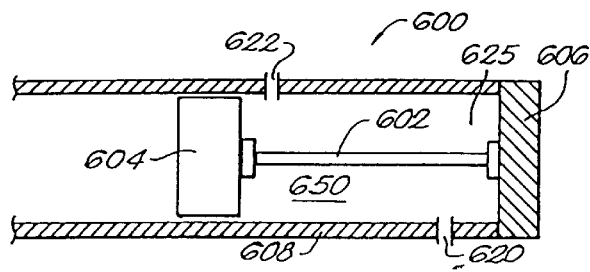

FIG. 8B shows an elongate tissue maturation apparatus 600 mounting a tissue 602 between a piston 604. The tissue is disposed for translation in a longitudinal bore formed by housing walls 608 of the apparatus 600. An endcap 606 seals one end of the longitudinal bore. The sidewalls of the chamber have an input fluid bore 622 and an output fluid bore formed therein. The piston is devoid of apertures. The fluid ports 620 and 622 allow for a selected flow of maturation fluid 650 in the bore volume 625, and for providing a selected fluid pressure in the bore volume 625 for applying a longitudinal stress to the biopolymer tissue 602. The illustrated apparatus 600 operates in a manner similar to FIG. 3.

Figure 8C:
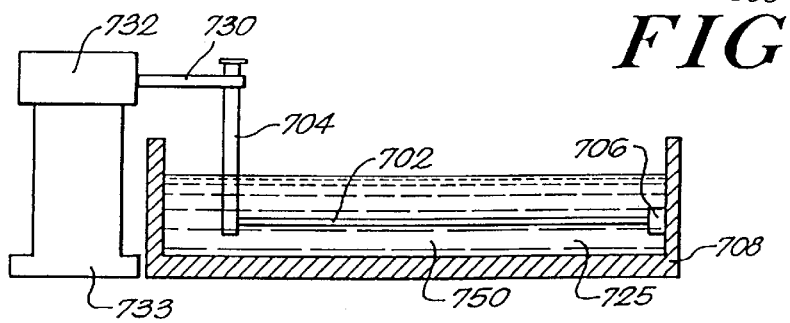

FIG. 8C shows an "open" apparatus 700 for maturing an elongate biopolymer tissue 702 mounted between a mounting element 706 at one end and a vertical rod 704 at the other. The mounting element 706 is attached to an end wall of a reservoir 708, and the vertical rod 704 is coupled to a horizontal rod 730 of a reciprocating electromechanical actuator 732. The actuator 732 is supported by a stand 733, and the reservoir houses a maturation fluid 750. The actuator reciprocates the rods 730 and 704 so as to apply selected forces to the tissue. The tissue can be selected to a longitudinal stress by the movement of the vertical rod in a longitudinal direction, as well as to selected shear forces from the contact between the liquid and the tissue during movement of the rod 704.

Figure 8D:
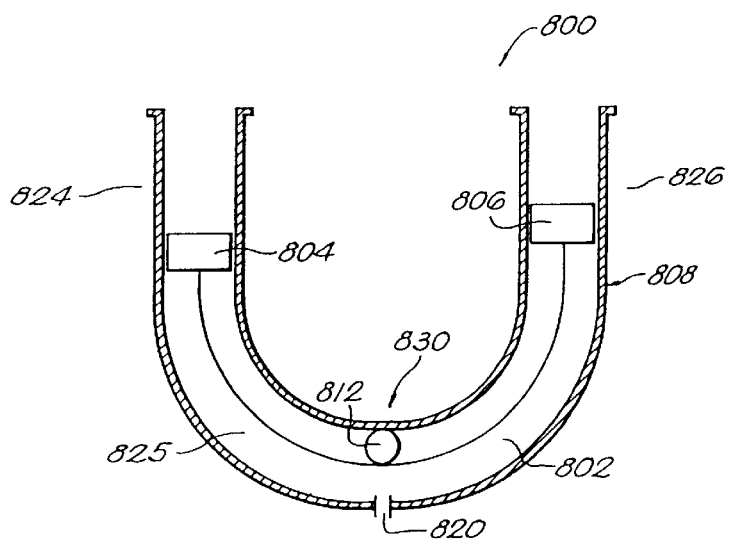

FIG. 8D illustrates another apparatus for maturing a biopolymer tissue 802 in the presence of a maturation fluid. The illustrated apparatus 800 includes a "U" shaped tube 808 which mounts within a bore 825 a pair of pistons 804 and 806, and between which the tissue extends. The pistons are disposed for travel within the straight sections 824 and 826 of the "U" shaped tube. The elongate tissue 802 is supported at a middle portion 830 of the tube by a support bearing 812. Movement of either piston places the tissue in contact with the support 830, which in turn exerts a transverse force on the tissue 802. Accordingly, the apparatus 800 can simultaneously provide both longitudinal stress and a transverse force on the biopolymer tissue 802. Fluid port 820 formed within the tube allows maturation fluid to escape from the bore 825. This arrangement hence forms a selected and variable fluid pressure that also exerts a longitudinal stress on the biopolymer tissue 802. Additional fluid ports (not shown) can be provided in the housing or in one or both of the pistons 804 and 806 for allowing a selected flow of maturation fluid 850 fluid into the bore 825 of the apparatus 800.

Transverse and frictional forces can be applied to the biopolymer tissues 502, 602, 702 and 802 shown in the alternative embodiments illustrated in FIGS. 8A through 8D using, as appropriate, the techniques and apparatus discussed in connection with FIGS. 5 through 7, with the foregoing magnetic techniques being preferably employed with the apparatus described in relation to FIGS. 8C and 8D.

It will thus be seen that the invention efficiently attains the objects set forth above, among those made apparent from the preceding description. Generally, disclosed herein are methods for exposing an elongate biopolymer tissue construct to a culturing, or maturation fluid, and for applying selected forces and/or stresses to the exposed tissue construct. The forces include frictional forces as well longitudinal stresses, i.e. placing the tissue under tension. The invention functions in part by conditioning tissue in vitro in a manner designed to simulate selected in vivo conditions, i.e., the conditions under which a tissue grows, remodels, and degrades, i.e., exposed to certain fluids, and subjected to certain stresses, such as tension.

Several embodiments of apparatus are disclosed for implementing the above techniques. However, these embodiments are intended as illustrative of apparatus for practicing the present invention and not as limiting. One of ordinary skill of the art, with knowledge of the present disclosure, can likely envision other embodiments, or variations of the disclosed embodiments, that encompass, and accomplish the purposes of, the present invention. Accordingly, these variations and embodiments are considered within the spirit and scope of the invention.

It is also to be understood that the following claims are to cover all generic and specific features of the invention described herein, and all statements of the scope of the invention which, as a matter of language, might be the to fall therebetween.

Having described the invention, what is claimed as new and desired to be secured by Letters Patent is:

1. A method for promoting the strengthening and maturation of a biopolymer tissue construct, comprising:
   positioning the biopolymer tissue construct within a maturation housing so as to extend along a longitudinal axis of the housing;
   exposing the biopolymer tissue to a maturation fluid; and
   applying a selected force to at least a portion of the tissue in a direction transverse to the longitudinal axis to strengthen and promote maturation of the tissue.

2. The method of claim 1, wherein the step of applying a transverse stress comprises the step of applying a stress within a range between about 0.2 Mpa and about 10 Mpa.

3. The method of claim 1, wherein the step of applying a transverse stress comprises cyclically applying transverse stress so as to stretch and relax the biopolymer tissue construct, the frequency of the cyclical application of the transverse stress chosen from the range of between about 1 and about 30 cycles per minute.

4. The method of claim 1, wherein the step of exposing the biopolymer tissue to a maturation fluid further comprises the step of immersing the biopolymer tissue construct in the maturation fluid.

5. The method of claim 1, wherein the step of exposing the biopolymer tissue construct to a maturation fluid further comprises the step of immersing the biopolymer tissue construct in the maturation fluid, the maturation fluid having a selected flow rate along the longitudinal axis of about 0 cc/min to about 5 cc/min.

6. The method of claim 1, wherein the step of exposing the biopolymer tissue to maturation fluid includes exposing the biopolymer tissue to ascorbic acid.

7. The method of claim 1, including the step of varying that portion of the tissue to which the force transverse to the longitudinal axis is applied.

8. The method of claim 7, wherein the step of varying the portion of the biopolymer tissue to which the force is applied includes varying, along the longitudinal axis, the portion of the tissue to which the transverse force is applied.

9. The method of claim 7, wherein the step of varying the portion of the biopolymer tissue to which the force is applied includes varying about a circumference of the tissue that portion of the tissue to which force is applied.

10. The method of claim 1, wherein applying a force transverse to the longitudinal axis includes applying a force in the range between about 0.5 g and about 20 g.

11. The method of claim 1, further comprising the step of seeding the biopolymer tissue construct with appropriate cells.

12. The method of claim 11, wherein said step of seeding further comprises the step of providing connective tissue type cells for seeding the biopolymer tissue construct.

13. The method of claim 12, further comprising the step of providing biological signals to the cells to mimic the natural bodily environment.

14. The method of claim 12, further comprising the step of providing biological signals to the cells for producing a replacement tissue more readily accepted by the body.

15. The method of claim 14, further comprising the step of promoting with said biological signals the secretion of extracellular matrix material and generating cell binding sites within the biopolymer tissue construct that attract specific cells from the body.

16. The method of claim 1, further comprising the step of forming the biopolymer tissue construct from collagen.

17. The method of claim 1, further comprising the step of providing a maturation fluid that resembles the naturally occurring fluid present in the bodily environment in which said biopolymer tissue construct tissue is used.

18. A method for promoting the strengthening and maturation of a biopolymer tissue construct, comprising:

positioning the biopolymer tissue construct within a maturation housing so as to extend along a longitudinal axis of the housing;

exposing the biopolymer tissue to a maturation fluid; and applying a frictional stress to at least a portion of an outer surface of the tissue to promote strengthening and maturation of the tissue.

19. The method of claim 18, including the step of varying that portion of the outer surface of the tissue to which the frictional force is applied.

20. The method of claim 19, including the step of varying, along the longitudinal axis, that portion of the outer surface of the tissue to which the frictional force is applied.

21. The method of claim 19, wherein the step of varying the portion of the surface of the biopolymer tissue to which the frictional force is applied includes varying about a circumference of the tissue that portion of the surface of the tissue to which the frictional force is applied.

22. The method of claim 18, wherein the step of applying a frictional stress comprises the step of applying a stress within a range between about 0.2 Mpa and about 10 Mpa.

23. The method of claim 18, wherein the step of applying a frictional stress comprises cyclically applying frictional stress so as to stretch and relax the biopolymer tissue construct, the frequency of the cyclical application of the frictional stress chosen from the range of between about 1 and about 30 cycles per minute.

24. The method of claim 18, wherein the step of exposing the biopolymer tissue to a maturation fluid further comprises the step of immersing the biopolymer tissue construct in the maturation fluid.

25. The method of claim 18, wherein the step of exposing the biopolymer tissue construct to a maturation fluid further comprises the step of immersing the biopolymer tissue construct in the maturation fluid, the maturation fluid having a selected flow rate along the longitudinal axis of about 0 cc/min to about 5 cc/min.

26. The method of claim 18, wherein the step of exposing the biopolymer tissue to maturation fluid includes exposing the biopolymer tissue to ascorbic acid.

27. The method of claim 18, including the step of varying that portion of the tissue to which the frictional force is applied.

28. The method of claim 27, wherein the step of varying the portion of the biopolymer tissue to which the force is applied includes varying, along the longitudinal axis, the portion of the tissue to which the frictional force is applied.

29. The method of claim 27, wherein the step of varying the portion of the biopolymer tissue to which the force is applied includes varying about a circumference of the tissue that portion of the tissue to which frictional force is applied.

30. The method of claim 18, wherein applying a frictional stress includes applying a force in the range between about 0.5 g and about 20 g.

31. The method of claim 18, further comprising the step of seeding the biopolymer tissue construct with appropriate cells.

32. The method of claim 31, wherein said step of seeding further comprises the step of providing connective tissue type cells for seeding the biopolymer tissue construct.

33. The method of claim 32, further comprising the step of providing biological signals to the cells to mimic the natural bodily environment.

34. The method of claim 32, further comprising the step of providing biological signals to the cells for producing a replacement tissue more readily accepted by the body.

35. The method of claim 34, further comprising the step of promoting with said biological signals the secretion of extracellular matrix material and generating cell binding sites within the biopolymer tissue construct that attract specific cells from the body.

36. The method of claim 18, further comprising the step of forming the biopolymer tissue construct from collagen.

37. The method of claim 18, further comprising the step of providing a maturation fluid that resembles the naturally occurring fluid present in the bodily environment in which said biopolymer tissue construct tissue is used.

38. A method for promoting the strengthening and maturation of a biopolymer tissue construct, comprising:

positioning the biopolymer tissue construct within a maturation housing so as to extend along a longitudinal axis of the housing;

exposing the biopolymer tissue to a maturation fluid; and applying a torsional force to at least a portion of the tissue to promote strengthening and maturation of the tissue.

39. The method of claim 38, wherein applying a torsional stress includes rotating, about the longitudinal axis, the first end of the biopolymer tissue relative the second end of the biopolymer tissue.

40. The method of claim 38, wherein the step of applying a torsional stress comprises the step of applying a stress within a range between about 0.2 Mpa and about 10 Mpa.

41. The method of claim 38, wherein the step of applying a torsional stress comprises cyclically applying torsional stress so as to stretch and relax the biopolymer tissue construct, the frequency of the cyclical application of the torsional stress chosen from the range of between about 1 and about 30 cycles per minute.

42. The method of claim 38, wherein the step of exposing the biopolymer tissue to a maturation fluid further comprises the step of immersing the biopolymer tissue construct in the maturation fluid.

43. The method of claim 38, wherein the step of exposing the biopolymer tissue construct to a maturation fluid further comprises the step of immersing the biopolymer tissue construct in the maturation fluid, the maturation fluid having a selected flow rate along the longitudinal axis of about 0 cc/min to about 5 cc/min.

44. The method of claim 38, wherein the step of exposing the biopolymer tissue to maturation fluid includes exposing the biopolymer tissue to ascorbic acid.

45. The method of claim 38, including the step of varying that portion of the tissue to which the torsional force is applied.

46. The method of claim 45, wherein the step of varying the portion of the biopolymer tissue to which the force is applied includes varying, along the longitudinal axis, the portion of the tissue to which the torsional force is applied.

47. The method of claim 45, wherein the step of varying the portion of the biopolymer tissue to which the force is applied includes varying about a circumference of the tissue that portion of the tissue to which torsional force is applied.

48. The method of claim 38, wherein applying a torsional stress includes applying a force in the range between about 0.5 g and about 20 g.

49. The method of claimed 38, further comprising the step of seeding the biopolymer tissue construct with appropriate cells.

50. The method of claim 49, wherein said step of seeding further comprises the step of providing connective tissue type cells for seeding the biopolymer tissue construct.

51. The method of claim 50, further comprising the step of providing biological signals to the cells to mimic the natural bodily environment.

52. The method of claim 50, further comprising the step of providing biological signals to the cells for producing a replacement tissue more readily accepted by the body.

53. The method of claim 52, further comprising the step of promoting with said biological signals the secretion of extracellular matrix material and generating cell binding sites within the biopolymer tissue construct that attract specific cells from the body.

54. The method of claim 38, further comprising the step of forming the biopolymer tissue construct from collagen.

55. The method of claim 38, further comprising the step of providing a maturation fluid that resembles the naturally occurring fluid present in the bodily environment in which said biopolymer tissue construct tissue is used.

* * * * *